United States Patent [19]

Burke et al.

[11] 4,080,381
[45] Mar. 21, 1978

[54] WATER SOLUBLE TERTIARY AMINE BORANES

[75] Inventors: Aaron R. Burke, Wexford; William V. Hough, Evans City, both of Pa.

[73] Assignee: Mine Safety Appliances Company, Pittsburgh, Pa.

[21] Appl. No.: 743,221

[22] Filed: Nov. 19, 1976

[51] Int. Cl.² ............... C09K 3/00; C25D 3/46; C25D 3/48; C07C 93/04
[52] U.S. Cl. ............... 260/584 B; 204/46 G; 252/188; 260/584 C
[58] Field of Search ........... 260/583 R, 584 R, 584 A, 260/584 B, 584 C

[56] References Cited
PUBLICATIONS

Adams et al., Chemical Abstracts, vol. 75, #147309g (1971).

Primary Examiner—Floyd D. Higel

[57] ABSTRACT

New water soluble ether substituted tertiary amine boranes are prepared by reaction of dimethylsulfide borane and an ether substituted tertiary amine of the formula

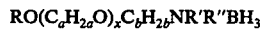

$$RO(C_aH_{2a}O)_xC_bH_{2b}NR'R''BH_3$$

wherein $a$ is zero or an integer from 1 to 3, $x$ is zero or an integer from 1 to 4, $b$ is an integer from 1 to 5 and R, R' and R" are alkyl groups containing up to 5 carbon atoms.

5 Claims, No Drawings

WATER SOLUBLE TERTIARY AMINE BORANES

CROSS REFERENCES

The amine boranes of the invention are useful in gold plating as described in the copending application, Ser. No. 743,220, of W. V. Hough, A. R. Burke and G. I. Hefferan, for Electroless Gold Plating Baths, filed on even date and of common ownership herewith.

BACKGROUND OF THE INVENTION

Amine boranes are used as reducing agents in both organic and inorganic reactions and processes. Amine boranes exhibit a wide range of reducing ability, it being well known that the reducing ability decreases as the number of carbon substituents on the amine nitrogen atom increases. Conventionally, amine boranes are selected with the appropriate reducing ability or strength to accomplish the desired reduction. Tertiary amine boranes are the mildest reducing agents among the family of amine boranes, but they have had only limited practical use since all known tertiary amine boranes are substantially insoluble in water.

SUMMARY OF THE INVENTION

It is an object of this invention to provide water soluble tertiary amine boranes and a method for preparing them. The water soluble compounds of the invention are ether substituted amine borane of the formula $$RO(C_aH_{2a}O)_xC_bH_{2b}NR'R'' \ BH_3$$

in which
 a is zero or an integer,
 x is zero or an integer,
 b is an integer, and
 R, R' and R" are alkyl groups.

Tertiary amine boranes having a simple ether substituent (where $a$ is zero) are soluble in water, sufficient for use as a reducing agent in aqueous room temperature reactions, while those having a polyether substituent (where $a$ is an integer) are much more soluble. Although R, R' and R" may be any alkyl group, most readily available amines and ethers have lower alkyl groups containing up to five carbon atoms and, in the case of polyethers, up to five ether oxygen atoms, usually polymethylene, polyethylene or polypropylene glycol dialkyl ethers. Ether substituted amines can be derived from these materials by conventional organic synthesis. For example a halogen substituted amine and a metal alkoxide can be reacted according to $$RO(C_aH_{2a}O)M + XC_bH_{2b}NR'R'' \rightarrow$$
$$RO(C_aH_{2a}O)_xC_bH_{2b}NR'R'' + MX$$

wherein M is alkali metal and X is a halogen. The new amine boranes are prefereably prepared by reaction of the appropriate ether substituted amine with dimethylsulfide borane according to the equation $$RO(C_aH_{2a}O)_xC_bH_{2b}NR'R'' + (CH_3)_2SBH_3 \rightarrow =$$
$$RO(C_aH_{2a}O)_xC_bH_{2b}NR'R''BH_3 + (CH_3)_2S$$

DESCRIPTION OF THE PREFERRED EMBODIMENTS

EXAMPLE 1

Two Hundred milliliters of distilled dimethylsulfide (DMS) and 122.5 g (523.5 mmol) of $CH_3O(C_2H_4O)_3C_2H_4N(CH_3)_2$ were added to a one liter three necked flask equipped with a magnetic stirring bar, a thermometer and a 250 ml pressure equalizing dropping funnel. 41.4 grams (523.5 mmol) of dimethylsulfide borane (DMSB) was added to the funnel. The DMSB was added dropwise over the next hour while maintaining the reaction vessel temperature between 7°-15° C with ice water cooling. After the reaction was complete, the DMS solvent was removed under vacuum. The remaining liquid amine borane was tested for water solubility and found to be very soluble in water.

EXAMPLE 2

(1) 62.0 g (530 mmol) of $CH_3CH_2OC_2H_4N(CH_3)_2$ and 41.7 g (530 mmol) of DMSB were reacted in the same manner as example 1. The resulting liquid amine borane had a solubility of 17 g/l in water at 25° C.

EXAMPLE 3

33.7 g (229.2 mmol) of $CH_3OC_2H_4OC_2H_4N(CH_3)_2$ and 18.1 g (230 mmol) of DMSB were reacted in the same manner as example (1). The resulting liquid amine borane has an approximate water solubility of 200 g/l of solution.

EXAMPLE 4

113.2 g (1099 mmol) of $CH_3OC_2H_4N(CH_3)_2$ and 87.3 g (1099 mmol) DMSB were reacted in the same manner as example 1. The liquid amine borane has a limiting solubility of 38 g/l of solution in water. Inert solvents, such as hydrocarbon or ether solvents, can be used partially or wholly in place of the DMS. Temperature, pressure and reaction proportions are not critical, although it is generally most convenient to use stoichiometric proportions at atmospheric pressure and room temperature or below.

The amine boranes of this invention are useful as reducing agents in aqueous solutions. For example, solutions of gold salts are reduced by the water soluble amine boranes to plate gold on a catalytically active surface contacted with the solution, as is more fully described in the above referenced co pending application. To illustrate, the pH of one hundred ml of a 3.0 g/l solution of $KAuCl_4$ was raised to 12.5 by the addition of NaOH. In a separate beaker, the pH of 100 ml of a 2.00g/l solution of $CH_3OCH_2CH_2N(CH_3)_2:BH_3$ was also raised to 12.5 by the addtion of NaOH. These two solutions were mixed with stirring and the resulting solution remained clear and stable. A palladium chloride activated substrate of nickel plate was immersed in the stirred bath for one hour at room temperature. Plating was noted immediately and after one hour a weight increase of 0.34 mg/cm² was measured.

While the preferred embodiments of the invention have been described with particularity, it will be recognized the invention may be otherwise embodied with the scope of the claim.

We claim:

1. A water soluble tertiary amine borane of the formula $$RO(C_aH_{2a}O)_xC_bH_{2b}NR'R''BH_3$$

wherein $a$ is zero or an integer from 1 to 3, $x$ is zero or an integer from 1 to 4, $b$ is an integer from 1 to 5 and R, R' and R" are alkyl groups containing up to 5 carbon atoms.
2. The compound, $CH_3O(C_2H_4O)_3C_2H_4N(CH_3)_2BH_3$
3. The compound, $CH_3CH_2OC_2H_4N(CH_3)_2BH_3$
4. The compound, $CH_3OC_2H_4OC_2H_4N(CH_3)_2BH_3$
5. The compound, $CH_3OC_2H_4N(CH_3)_2BH_3$.